(12) United States Patent
Seadeek

(10) Patent No.: US 10,414,748 B2
(45) Date of Patent: Sep. 17, 2019

(54) CRYSTALLINE FORMS OF 1-((2R,4R)-2-(1H-BENZO[D]IMIDAZOL-2-YL)-1-METHYLPIPERIDIN-4-YL)-3-(4-CYANOPHENYL)UREA MALEATE

(71) Applicant: PFIZER INC., New York, NY (US)

(72) Inventor: Christopher Scott Seadeek, West Lafayette, IN (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/567,433

(22) PCT Filed: Apr. 13, 2016

(86) PCT No.: PCT/IB2016/052107
§ 371 (c)(1),
(2) Date: Oct. 18, 2017

(87) PCT Pub. No.: WO2016/170451
PCT Pub. Date: Oct. 27, 2016

(65) Prior Publication Data
US 2018/0086731 A1    Mar. 29, 2018

Related U.S. Application Data

(60) Provisional application No. 62/152,108, filed on Apr. 24, 2015.

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC .................................................. C07D 401/04
See application file for complete search history.

(56) References Cited

U.S. PATENT DOCUMENTS

| | | |
|---|---|---|
| 8,148,401 B2 | 4/2012 | Munchhof et al. |
| 8,431,597 B2 | 4/2013 | Munchhof et al. |
| 2009/0005416 A1 | 1/2009 | Munchhof et al. |

FOREIGN PATENT DOCUMENTS

WO    2009004427 A2    1/2009

OTHER PUBLICATIONS

Berge et al., Journal of Pharmaceutical Sciences, vol. 66, No. 1, Jan. 1977, pp. 1-19.*
Munchhof, et al., "Discovery of PF-04449913, a Potent and Orally Bioavailable Inhibitor of Smoothened", Medicinal Chemistry Letters, 2012, 106-111, 3.
Peng et al., "Development of a Concise, Asymmetric Synthesis of a Smoothened Receptor (SMO) Inhibitor: Enzymatic Transamination of a 4-Piperidinone with Dynamic Kinetic Resolution", Organic Letters, 2014, 860-863, 16.
Recommended INN: List 73, WHO Drug Information, 2015, vol. 29, No. 1, p. 89.
International Search Report dated Jun. 28, 2016 for International application No. PCT/IB2016/052107, filed Apr. 13, 2016.
Written Opinion of the International Searching Authority for International application No. PCT/IB2016/052107, filed Apr. 13, 2016.
Anderson et al., "Preparation of Water-Soluble Compounds Through Salt Formation", in C. G. Wermuth Practice of Medicinal Chemistry, second volume, Technomics, published on Sep. 25, 1999, pp. 347-349. Translation of cited pages included with Article.
Solvent Handbook, first edition, Koudansya, published on Sep. 1, 1985, pp. 47-51. Translation of cited pages included with Article.
"4. Separation and purification", in Jikken Kagaku Kouza 1, Kihonsousa 1, The Chemical Society of Japan, fouth edition, Maruzen, published on Apr. 5, 1996, p. 184-189. Translation of cited pages included with Article.

* cited by examiner

*Primary Examiner* — Rebecca L Anderson
(74) *Attorney, Agent, or Firm* — Victoria C. Summers

(57) ABSTRACT

This invention relates to a crystalline form of 1-((2R,4R)-2-(1H-benzo[d]imidazol-2-yl)-1-methylpiperidin-4-yl)-3-(4-cyanophenyl)urea maleate, and to pharmaceutical compositions thereof, to intermediates and methods for the production and isolation of such crystalline forms and compositions, and to methods of using such crystalline forms and compositions in the treatment of abnormal cell growth in mammals, especially humans.

18 Claims, 5 Drawing Sheets

CRYSTALLINE FORMS OF 1-((2R,4R)-2-(1H-BENZO[D]IMIDAZOL-2-YL)-1-METHYLPIPERIDIN-4-YL)-3-(4-CYANOPHENYL)UREA MALEATE

CROSS-REFERENCE TO RELATED APPLICATIONS

This Application is the national stage filing under 35 U.S.C. 371 of Patent Cooperation Treaty Patent Application No. PCT/IB2016/052107, filed Apr. 13, 2016, which claims the benefit of priority from U.S. Provisional Application No. 62/152,108 filed Apr. 24, 2015, the contents of each of which are hereby incorporated by reference in their entirety.

FIELD OF THE INVENTION

This invention relates to a crystalline form of 1-((2R,4R)-2-(1H-benzo[d]imidazol-2-yl)-1-methylpiperidin-4-yl)-3-(4-cyanophenyl)urea maleate and to pharmaceutical compositions thereof, to intermediates and methods for the production and isolation of such crystalline forms and compositions, and to methods of using such crystalline forms and compositions in the treatment of abnormal cell growth in mammals, especially humans.

BACKGROUND OF THE INVENTION

The monomaleate salt of 1-((2R,4R)-2-(1H-benzo[d]imidazol-2-yl)-1-methylpiperidin-4-yl)-3-(4-cyanophenyl)urea has the structure of Formula (I):

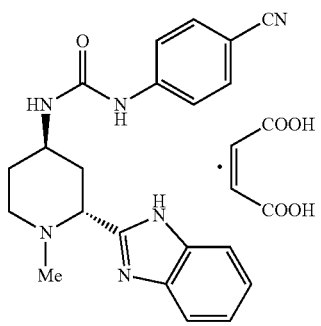

(I)

The compound 1-((2R,4R)-2-(1H-benzo[d]imidazol-2-yl)-1-methylpiperidin-4-yl)-3-(4-cyanophenyl)urea (PF-04449913) has been assigned the International Nonproprietary Name (INN) glasdegib, as described in *WHO Drug Information*, Vol. 29, No. 1, page 89 (2015), referencing the alternative chemical name N-[(2R,4R)-2-(1H-benzoimidazol-2-yl)-1-methylpiperidin-4-yl]-N'-(4-cyanophenyl)urea. The maleate salt of Formula (I) may also be referred to herein as 1-((2R,4R)-2-(1H-benzo[d]imidazol-2-yl)-1-methylpiperidin-4-yl)-3-(4-cyanophenyl)urea maleate or glasdegib maleate.

Preparation of glasdegib as a hydrochloride salt is described in International Patent Application No. PCT/IB2008/001575, published as WO 2009/004427, and in U.S. Pat. Nos. 8,148,401 and 8,431,597, the contents of each of which are incorporated herein by reference in their entirety.

Glasdegib is an inhibitor of the smoothened receptor (Smo), a component of the hedgehog (Hh) signaling pathway that is a potential therapeutic target in a number of human cancers, in particular hematologic malignancies including acute myeloid leukemia (AML), acute lymphoblastic leukemia (ALL), chronic myelomonocytic leukemia (CMML), myelofibrosis (MF) and myelodysplastic syndromes (MDS). The discovery of glasdegib and its preparation as a dihydrochloride monohydrate salt has been described by Munchhof et al. (*Med. Chem., Lett*, 2012, 3:106-111). A process for the asymmetric synthesis of glasdegib has been described by Peng et al. (*Org. Lett.*, 2014, 16:860-863).

The present invention provides crystalline glasdegib maleate having improved properties, such as improved chemical and thermal stability upon storage, and decreased hygroscopicity, while maintaining chemical and enantiomeric stability.

The invention also provides a crystalline glasdegib imidazole complex (1:1) and a crystalline glasdegib (S)-mandelate salt, which are useful for the preparation of glasdegib maleate and other salts in high yield and with high chemical purity.

SUMMARY OF THE INVENTION

Each of the embodiments described below can be combined with any other embodiment described herein not inconsistent with the embodiment with which it is combined.

In one aspect, the invention provides a crystalline form of glasdegib maleate. In a particular aspect, the invention provides a crystalline glasdegib maleate (Form 1), as further described herein.

In particular embodiments of each of the aspects of the invention, the crystalline glasdegib maleate (Form 1) is characterized by one or more of the following methods: (1) powder X-ray diffraction (PXRD) (2θ); (2) Raman spectroscopy (cm$^{-1}$); or (3) $^{13}$C solid state NMR spectroscopy (ppm).

In another aspect, the invention provides crystalline glasdegib maleate (Form 1), which is characterized by having:

(1) a powder X-ray diffraction (PXRD) pattern (2θ) comprising: (a) one, two, three, four, five, or more than five peaks selected from the group consisting of the peaks in Table 1 in °2θ±0.2 °2θ; (b) one, two or three peaks selected from the group consisting of the characteristic peaks in Table 1 in °2θ±0.2 °2θ; or (c) peaks at 2θ values essentially the same as shown in FIG. 1; or (2) a Raman spectrum comprising: (a) one, two, three, four, five, or more than five wavenumber (cm$^{-1}$) values selected from the group consisting of the values in Table 2 in cm$^{-1}$±2 cm$^{-1}$; (b) one, two, three, four, five, or more than five wavenumber (cm$^{-1}$) values selected from the group consisting of the characteristic values in Table 2 in cm$^{-1}$±2 cm$^{-1}$; or (c) wavenumber (cm$^{-1}$) values essentially the same as shown in FIG. 2; or (3) a $^{13}$C solid state NMR spectrum (ppm) comprising: (a) one, two, three, four, five, or more than five resonance (ppm) values selected from the group consisting of the values in Table 3 in ppm±0.2 ppm; (b) one, two or three resonance (ppm) values selected from the group consisting of the characteristic values in Table 3 in ppm±0.2 ppm; or (c) resonance (ppm) values essentially the same as shown in FIG. 3;

or a combination of any two or three of the foregoing embodiments (1)(a)-(c), (2)(a)-(c) or (3)(a)-(c), provided they are not inconsistent with each other.

In another aspect, the invention further provides a pharmaceutical composition comprising a crystalline glasdegib maleate (Form 1), according to any of the aspects or embodiments described herein, and a pharmaceutically acceptable excipient.

In another aspect, the invention provides a method of treating abnormal cell growth in a mammal, including a human, comprising administering to the mammal a therapeutically effective amount of crystalline glasdegib maleate (Form 1).

In another aspect, the invention provides a method of treating abnormal cell growth in a mammal, including a human, comprising administering to the mammal a therapeutically effective amount of a pharmaceutical composition of the present invention comprising a crystalline glasdegib maleate (Form 1), according to any of the aspects or embodiments described herein.

DETAILED DESCRIPTION OF THE INVENTION

Figure 1:
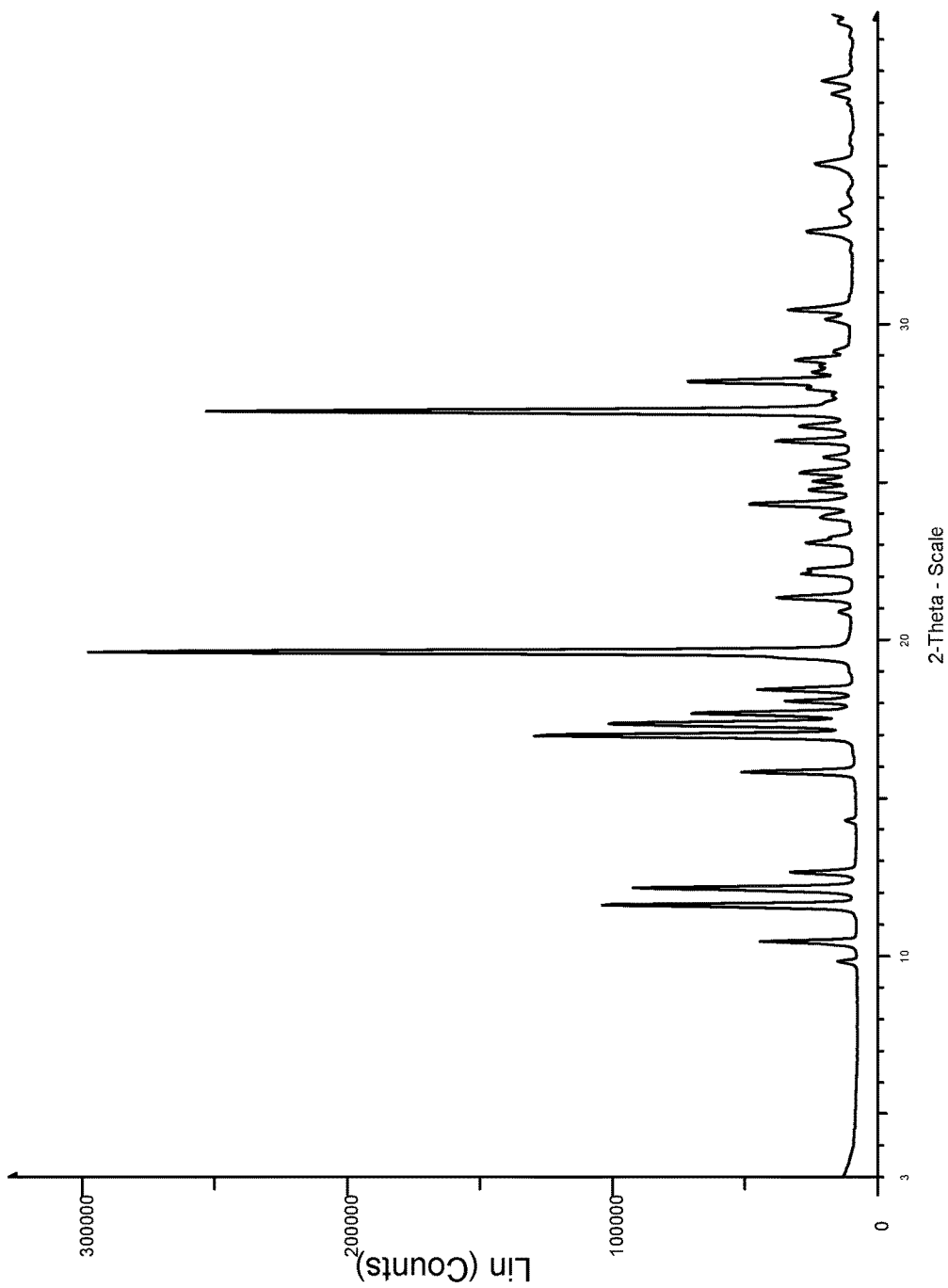
FIG. 1. PXRD pattern of crystalline glasdegib maleate (Form 1).

The present invention may be understood more readily by reference to the following detailed description of the embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

As used herein, unless otherwise indicated, the term "abnormal cell growth" refers to cell growth that is independent of normal regulatory mechanisms (e.g., loss of contact inhibition).

As used herein, unless otherwise indicated, the term "treat" or "treating" means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "about" as used herein means having a value falling within an accepted standard of error of the mean, when considered by one of ordinary skill in the art, for example ±20%, preferably ±10% or more preferably ±5% of the mean.

As used herein, the term "essentially the same" means that variability typical for a particular method is taken into account. For example, with reference to X-ray diffraction peak positions, the term "essentially the same" means that typical variability in peak position and intensity are taken into account. One skilled in the art will appreciate that the peak positions (2θ) will show some variability, typically as much as ±0.2°. Further, one skilled in the art will appreciate that relative peak intensities will show inter-apparatus variability as well as variability due to degree of crystallinity, preferred orientation, prepared sample surface, and other factors known to those skilled in the art and should be taken as qualitative measures only. Similarly, Raman spectrum wavenumber ($cm^{-1}$) values show variability, typically as much as ±2 $cm^{-1}$, while $^{13}C$ and $^{19}F$ solid state NMR spectrum (ppm) show variability, typically as much as ±0.2 ppm.

The term "crystalline" as used herein, means having a regularly repeating arrangement of molecules or external face planes. Crystalline forms may differ with respect to thermodynamic stability, physical parameters, x-ray structure and preparation processes.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

In some embodiments of each of the aspects of the invention, the crystalline glasdegib maleate (Form 1) is characterized by its powder X-ray diffraction (PXRD) pattern. In other embodiments of each of the aspects of the invention, the crystalline glasdegib maleate (Form 1) is characterized by its Raman spectrum. In other embodiments of each of the aspects of the invention, the crystalline glasdegib maleate (Form 1) is characterized by its $^{13}C$ solid state NMR spectrum.

In further embodiments, the crystalline form is characterized by a combination of two or more of these methods.

Crystalline Glasdegib Maleate (Form 1)

In one aspect, the invention provides a crystalline glasdegib maleate (Form 1).

In some embodiments, glasdegib maleate (Form 1) has a PXRD pattern comprising a peak at 2θ value of: 11.6 °2θ±0.2 °2θ. In another embodiment, Form 1 has a PXRD pattern comprising a peak at 2θ value of: 12.1 °2θ±0.2 °2θ. In another embodiment, Form 1 has a PXRD pattern comprising a peak at 2θ value of: 19.6 °2θ±0.2 °2θ. In another embodiment, Form 1 has a PXRD pattern comprising a peak at 2θ value of: 17.0 °2θ±0.2 °2θ. In another embodiment, Form 1 has a PXRD pattern comprising a peak at 2θ value of: 17.7 °2θ±0.2 °2θ. In another embodiment, Form 1 has a PXRD pattern comprising peaks at 2θ values of: 11.6 and 12.1 °2θ±0.2 °2θ. In another embodiment, Form 1 has a PXRD pattern comprising peaks at 2θ values of: 11.6 and 19.6 °2θ±0.2 °2θ. In another embodiment, Form 1 has a PXRD pattern comprising peaks at 2θ values of: 12.1 and 19.6 °2θ±0.2 °2θ. In another embodiment, Form 1 has a PXRD pattern comprising peaks at 2θ values of: 11.6, 12.1 and 19.6 °2θ±0.2 °2θ. In yet another embodiment, Form 1 has a PXRD pattern comprising peaks at 2θ values of: 11.6, 12.1, 17.0, 17.7 and 19.6 °2θ±0.2 °2θ.

In specific embodiments, glasdegib maleate (Form 1) has a PXRD pattern comprising: (a) one, two, three, four, five, or more than five peaks selected from the group consisting of the peaks in Table 1 in °2θ±0.2 °2θ; (b) one, two, three, four, five or six characteristic peaks selected from the group consisting of the peaks in Table 1; or (c) peaks at 2θ values essentially the same as shown in FIG. 1.

In some embodiments, glasdegib maleate (Form 1) has a Raman spectrum comprising wavenumber ($cm^{-1}$) value of: 2219 $cm^{-1}$±2 $cm^{-1}$. In other embodiments, Form 1 has a Raman spectrum comprising wavenumber ($cm^{-1}$) value of: 1612 $cm^{-1}$±2 $cm^{-1}$. In another embodiment, Form 1 has a Raman spectrum comprising wavenumber (cm$^{-1}$) value of: 1534 cm$^{-1}$±2 cm$^{-1}$. In another embodiment, Form 1 has a Raman spectrum comprising wavenumber (cm$^{-1}$) value of: 1175 cm$^{-1}$±2 cm$^{-1}$. In other embodiments, Form 1 has a Raman spectrum comprising wavenumber (cm$^{-1}$) values of: 1612 and 2219 cm$^{-1}$±2 cm$^{-1}$. In other embodiments, Form 1 has a Raman spectrum comprising wavenumber (cm$^{-1}$) values of: 1534 and 2219 cm$^{-1}$±2 cm$^{-1}$. In further embodiments, Form 1 has a Raman spectrum comprising wavenumber (cm$^{-1}$) values of: 1534, 1612 and 2219 cm$^{-1}$±2 cm$^{-1}$. In further embodiments, Form 1 has a Raman spectrum comprising wavenumber (cm$^{-1}$) values of: 1175, 1534, 1612 and 2219 cm$^{-1}$±2 cm$^{-1}$.

Figure 2:
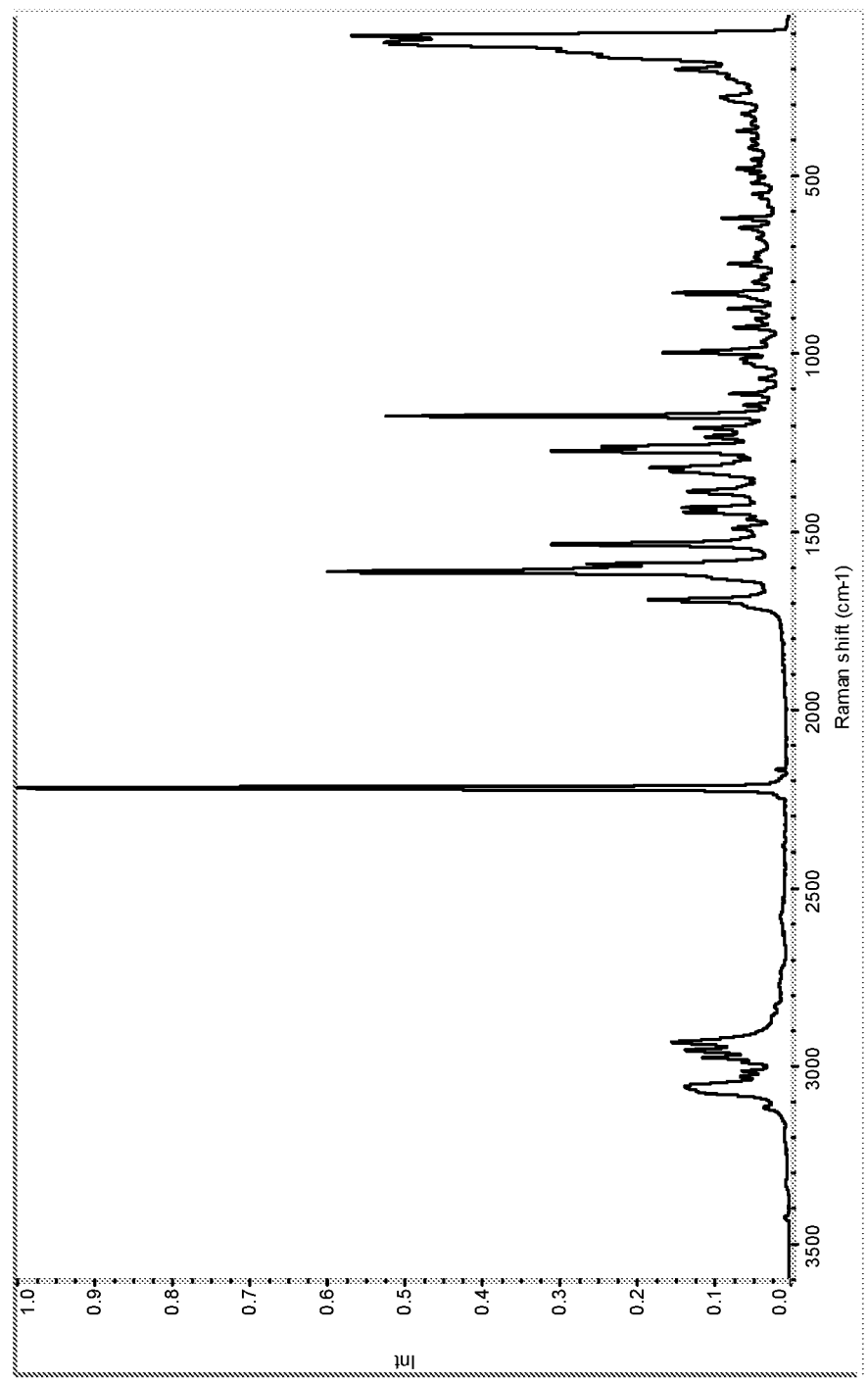
FIG. 2. FT-Raman spectrum of crystalline glasdegib maleate (Form 1).

In specific embodiments, glasdegib maleate (Form 1) has a Raman spectrum comprising: (a) one, two, three, four, five, or more than five wavenumber (cm$^{-1}$) values selected from the group consisting of the values in Table 2 in cm$^{-1}$±2 cm$^{-1}$; (b) one, two, three, four, five, or more than five wavenumber (cm$^{-1}$) values selected from the group consisting of the characteristic values in Table 2 in cm$^{-1}$±2 cm$^{-1}$; or (c) wavenumber (cm$^{-1}$) values essentially the same as shown in FIG. 2.

In some embodiments, glasdegib maleate (Form 1) has a $^{13}$C solid state NMR spectrum comprising the resonance (ppm) values of: 57.8 ppm±0.2 ppm. In another embodiment, Form 1 has a $^{13}$C solid state NMR spectrum comprising the resonance (ppm) values of: 134.8 ppm±0.2 ppm. In another embodiment, Form 1 has a $^{13}$C solid state NMR spectrum comprising the resonance (ppm) values of: 144.7 ppm±0.2 ppm. In another embodiment, Form 1 has a $^{13}$C solid state NMR spectrum comprising the resonance (ppm) values of: 148.3 ppm±0.2 ppm. In another embodiment, Form 1 has a $^{13}$C solid state NMR spectrum comprising the resonance (ppm) values of: 57.8 and 134.8 ppm±0.2 ppm. In another embodiment, Form 1 has a $^{13}$C solid state NMR spectrum comprising the resonance (ppm) values of: 57.8 and 144.7 ppm±0.2 ppm. In another embodiment, Form 1 has a $^{13}$C solid state NMR spectrum comprising the resonance (ppm) values of: 57.8 and 148.3 ppm±0.2 ppm. In another embodiment, Form 1 has a $^{13}$C solid state NMR spectrum comprising the resonance (ppm) values of: 134.8 and 144.7 ppm±0.2 ppm. In another embodiment, Form 1 has a $^{13}$C solid state NMR spectrum comprising the resonance (ppm) values of: 134.8 and 148.3 ppm±0.2 ppm. In another embodiment, Form 1 has a $^{13}$C solid state NMR spectrum comprising the resonance (ppm) values of: 144.7 and 148.3 ppm±0.2 ppm. In a further embodiment, Form 1 has a $^{13}$C solid state NMR spectrum comprising the resonance (ppm) values of: 57.8, 134.8 and 144.7 ppm±0.2 ppm. In a further embodiment, Form 1 has a $^{13}$C solid state NMR spectrum comprising the resonance (ppm) values of: 57.8, 134.8 and 148.3 ppm±0.2 ppm. In a further embodiment, Form 1 has a $^{13}$C solid state NMR spectrum comprising the resonance (ppm) values of: 57.8, 134.8, 144.7 and 148.3 ppm±0.2 ppm.

Figure 3:
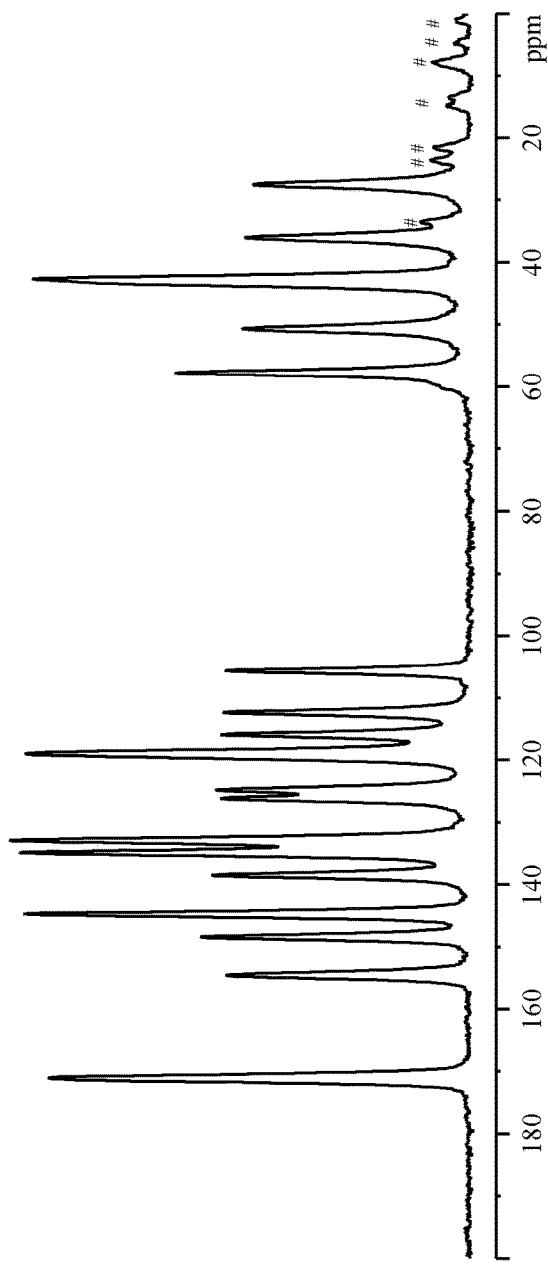
FIG. 3. $^{13}C$ solid state NMR spectrum of crystalline glasdegib maleate (Form 1).

In specific embodiments, glasdegib maleate (Form 1) has a $^{13}$C solid state NMR spectrum (ppm) comprising: (a) one, two, three, four, five, or more than five resonance (ppm) values selected from the group consisting of the values in Table 3 in ppm±0.2 ppm; (b) one, two or three resonance (ppm) values selected from the group consisting of the characteristic values in Table 3 in ppm±0.2 ppm; or (c) resonance (ppm) values essentially the same as shown in FIG. 3.

In further embodiments, glasdegib maleate (Form 1) is characterized by a combination of any two or three of the embodiments described above with respect to Form 1 that are not inconsistent with each other. Exemplary embodiments that may be used to uniquely characterize the crystalline Form 1 are provided below.

In one embodiment, Form 1 has: (a) a powder X-ray diffraction pattern comprising a peak at a 2θ value of: 11.6 and 12.1 °2θ±0.2 °2θ; and (b) a Raman spectrum comprising wavenumber (cm$^{-1}$) values of: 1612 and 2219 cm$^{-1}$±2 cm$^{-1}$.

In one embodiment, Form 1 has: (a) a powder X-ray diffraction pattern comprising a peak at a 2θ value of: 11.6 and 12.1 °2θ±0.2 °2θ; (b) a Raman spectrum comprising wavenumber (cm$^{-1}$) values of: 1612 and 2219 cm$^{-1}$±2 cm$^{-1}$; and (c) a $^{13}$C solid state NMR spectrum comprising a resonance (ppm) value of: 148.3 ppm±0.2 ppm.

In one another embodiment, Form 1 has: (a) a Raman spectrum comprising wavenumber (cm$^{-1}$) values of: 1612 and 2219 cm$^{-1}$±2 cm$^{-1}$; and (b) a $^{13}$C solid state NMR spectrum comprising a resonance (ppm) value of: 148.3 ppm±0.2 ppm.

In one embodiment, Form 1 has: (a) a powder X-ray diffraction pattern comprising a peak at a 2θ value of: 11.6 and 19.6 °2θ±0.2 °2θ; and (b) a $^{13}$C solid state NMR spectrum comprising a resonance (ppm) value of: 148.3 ppm±0.2 ppm.

In a further embodiment, Form 1 has: (a) a powder X-ray diffraction pattern comprising a peak at a 2θ value of: 19.6 °2θ±0.2 °2θ; (b) a Raman spectrum comprising wavenumber (cm$^{-1}$) values of: 2219 cm$^{-1}$±2 cm$^{-1}$; and (c) a $^{13}$C solid state NMR spectrum comprising a resonance (ppm) value of: 148.3 ppm±0.2 ppm.

In another aspect, the invention provides glasdegib as a 1:1 complex with imidazole. The imidazole complex is isolable in high chemical yield and purity and may be useful to purge impurities formed during chemical synthesis prior to formation of glasdegib maleate. In a further aspect, the invention provides a process for preparing glasdegib maleate comprising treating the glasdegib imidazole complex (1:1) with maleic acid, thereby providing the salt. In another aspect, the invention provides glasdegib maleate (Form 1) prepared from the glasdegib imidazole complex according to the process described.

In another aspect, the invention provides the glasdegib (S)-mandelate salt. The mandelate salt is isolable in high chemical yield and purity and may also be useful to purge impurities formed during chemical synthesis. The mandelate salt can be prepared in situ during the final isolation and purification of the compounds or by separately reacting glasdegib free base with mandelic acid and isolating the salt thus formed. Thereafter, the salt may be reconverted to the free base form and then reacted with a sufficient amount of maleic acid to produce the glasdegib maleate salt in the conventional manner.

In another aspect, the invention provides a pharmaceutical composition comprising a crystalline glasdegib maleate (Form 1) according to any of the aspects or embodiments described herein, and a pharmaceutically acceptable excipient.

Pharmaceutical compositions of the present invention may, for example, be in a form suitable for oral administration as a tablet, capsule, pill, powder, sustained release formulations, solution, or suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and an active pharmaceutical ingredient. In addition, it may include other medicinal or pharmaceutical agents, carriers, adjuvants, etc.

Exemplary parenteral administration forms include solutions or suspensions containing active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

EXAMPLES

The examples and preparations provided below further illustrate and exemplify particular aspects and embodiments of the invention. It is to be understood that the scope of the present invention is not limited by the scope of the following examples.

General Method 1. Powder X-Ray Diffraction (PXRD)

Powder X-ray diffraction analysis was conducted using a Bruker AXS D8 ADVANCE diffractometer equipped with a Cu radiation source (K-α average). The system is equipped with a 2.5 axial Soller slits on the primary side. The secondary side utilizes 2.5 axial Soller slits and motorized slits. Diffracted radiation was detected by a Lynx Eye XE detector. The X-ray tube voltage and amperage were set to 40 kV and 40 mA respectively. Data was collected in the Theta-Theta goniometer at the Cu wavelength from 3.0 to 40.0 degrees 2-Theta using a step size of 0.037 degrees and a step time of 1920 seconds. Samples were prepared by placing them in a low background holder and rotated during collection. Data were collected using Bruker DIFFRAC Plus software (Version 9.0.0.2) and analysis was performed by EVA diffract plus software.

The PXRD data file was not processed prior to peak searching. Using the peak search algorithm in the EVA software, peaks selected with a threshold value of 1 and a width value of 0.3 were used to make preliminary peak assignments. The output of automated assignments was visually checked to ensure validity and adjustments were manually made if necessary. Peaks with relative intensity of ≥2% were generally chosen. The peaks which were not resolved or were consistent with noise were not selected. A typical variability associated with the peak position from PXRD is +/−0.2° 2-Theta.

General Method 2. FT-Raman

Raman spectra were collected using a Nicolet NXR FT-Raman accessory attached to the FT-IR bench. The spectrometer is equipped with a 1064 nm Nd:YVO4 laser and a liquid nitrogen cooled Germanium detector. Prior to data acquisition, instrument performance and calibration verifications were conducted using polystyrene. Samples were analyzed in glass NMR tubes that were spun during spectral collection. The neat API spectra were collected using 0.5 W of laser power and 128 co-added scans. The collection range was 3700-50 cm-1. These spectra were recorded using 4 cm-1 resolution and Happ-Genzel apodization.

The intensity scale was normalized to 1 prior to peak picking. Peaks were manually identified using the Thermo Nicolet Omnic 7.3 software. Peak position was picked at the peak maximum, and peaks were only identified as such, if there was a slope on each side; shoulders on peaks were not included. For the neat API an absolute threshold of 0.015 with a sensitivity of 77 was utilized during peak picking. The peak position has been rounded to the nearest whole number using standard practice (0.5 rounds up, 0.4 rounds down). Peaks with normalized peak intensity between (1-0.75), (0.74-0.30), (0.29-0) were labeled as strong, medium and weak, respectively. It is expected that, since FT-Raman and dispersive Raman are similar techniques, peak positions reported herein for FT-Raman spectra would be consistent with those which would be observed using a dispersive Raman measurement, assuming appropriate instrument calibration. Utilizing the Raman method above, the variability associated with a spectral measurement is +/−2 cm$^{-1}$.

General Method 3. Solid State NMR

Solid state NMR (ssNMR) analysis was conducted at ambient temperature and pressure on a Bruker-BioSpin CPMAS probe positioned into a Bruker-BioSpin Avance III 500 MHz ($^1$H frequency) NMR spectrometer. The packed rotor was oriented at the magic angle and spun at 14.0 kHz. The carbon ssNMR spectrum was collected using a proton decoupled cross-polarization magic angle spinning (CP-MAS) experiment. A phase modulated proton decoupling field of 80-100 kHz was applied during spectral acquisition. The cross-polarization contact time was set to 2 ms and the recycle delay to 11 seconds. The number of scans was adjusted to obtain an adequate signal to noise ratio. The carbon spectrum was referenced using an external standard of crystalline adamantane, setting its upfield resonance to 29.5 ppm (as determined from neat TMS).

Automatic peak picking was performed using Bruker-BioSpin TopSpin version 3.2 software. Generally, a threshold value of 5% relative intensity was used to preliminary select peaks. The output of the automated peak picking was visually checked to ensure validity and adjustments were manually made if necessary. Although specific $^{13}$C solid state NMR peak values are reported herein there does exist a range for these peak values due to differences in instruments, samples, and sample preparation. This is common practice in the art of solid state NMR because of the variation inherent in peak values. A typical variability for a $^{13}$C chemical shift x-axis value is on the order of plus or minus 0.2 ppm for a crystalline solid. The solid state NMR peak heights reported herein are relative intensities. Solid state NMR intensities can vary depending on the actual setup of the CPMAS experimental parameters and the thermal history of the sample.

Example 1

Preparation of 1-((2R,4R)-2-(1H-benzo[d]imidazol-2-yl)-1-methylpiperidin-4-yl)-3-(4-cyanophenyl)urea imidazole Complex (1:1)

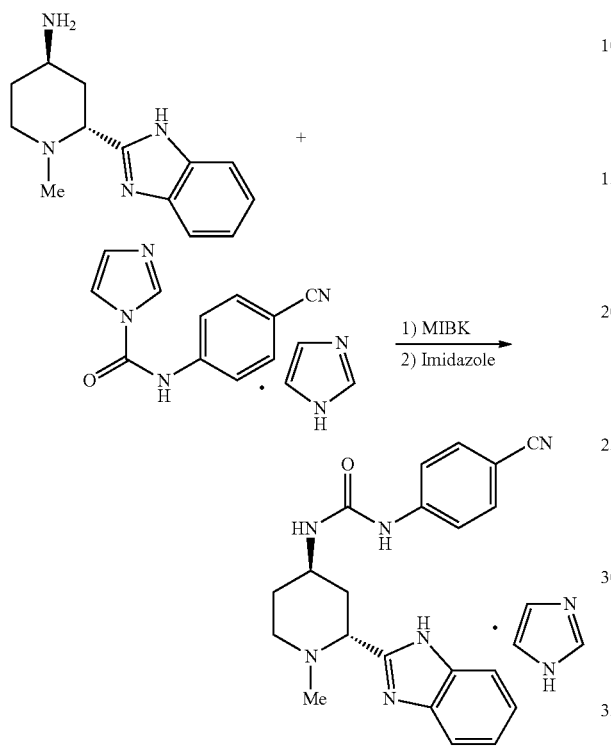

To a 250 mL reactor equipped with an overhead stirrer was added (2R,4R)-2-(1H-benzo[d]imidazol-2-yl)-1-methylpiperidin-4-amine (3.24 g, 14.1 mmol) (prepared according to Peng et al., *Org. Lett.* 2014, 16:860-863) as a solution in water (63 mL) containing 20% dimethylsulfoxide. To the solution was added 4-methyl-2-pentanone (methyl isobutyl ketone, MIBK) (91 mL) followed by N-(4-cyanophenyl)-1H-imidazole-1-carboxamide 1H-imidazole complex (1:1) (5.18 g, 17.6 mmol) (prepared according to Peng et al.). The reaction was heated at 45° C. for 1 hour. Diatomaceous earth (0.5 g, filter aid) was added and the biphasic mixture was filtered. The aqueous layer was removed and the organic layer was washed with water (33 mL). Imidazole (0.96 g, 14.1 mmol) was added along with additional 4-methyl-2-pentanone (18 mL). The solution was distilled to a final volume of 50 mL. The resulting slurry was filtered and washed with 4-methyl-2-pentanone (13 mL). The resulting solids were dried in a vacuum oven at 60° C. for 12 h to provide 1-((2R,4R)-2-(1H-benzo[d]imidazol-2-yl)-1-methylpiperidin-4-yl)-3-(4-cyanophenyl)urea imidazole complex (1:1) (4.55 g, 10.3 mmol, 73% yield). $^1$H NMR (400 MHz, DMSO-d$_6$): δ 12.38 (bs, 1H); 12.07 (bs, 1H); 8.94 (s, 1H); 7.67 (d, J=8.4 Hz, 2H); 7.65 (m, 1H); 7.58 (d, J=8.4 Hz, 2H); 7.55 (d, J=7.5 Hz, 1H); 7.43 (bd, J=7.5 Hz, 1H); 7.14 (m, 2H); 7.02 (s, 2H); 6.75 (d, J=7.1 Hz, 1H); 4.08 (m, 1H); 3.63 (dd, J=10.4, 3.2 Hz, 1H); 2.90 (dt, HJ=11.9, 4.2 Hz, 1H); 2.51 (p, J=1.8 Hz, 2H); 2.40 (td, J=11.7, 3.0 Hz, 1H); 2.06 (s, 3H); 2.03 (m, 1H); 1.92 (m, 1H); 1.86 (m, 1H); 1.72 (m, 1H); $^{13}$C NMR (101 MHz, DMSO) δ 156.17, 154.34, 145.2, 135.6, 133.7, 122.3, 121.5, 119.9, 118.9, 117.8, 111.7, 102.9, 59.1, 50.4, 44.2, 42.9, 36.5, 30.3.

Characterization of Alasdegib Imidazole Complex

PXRD Data

Figure 4:
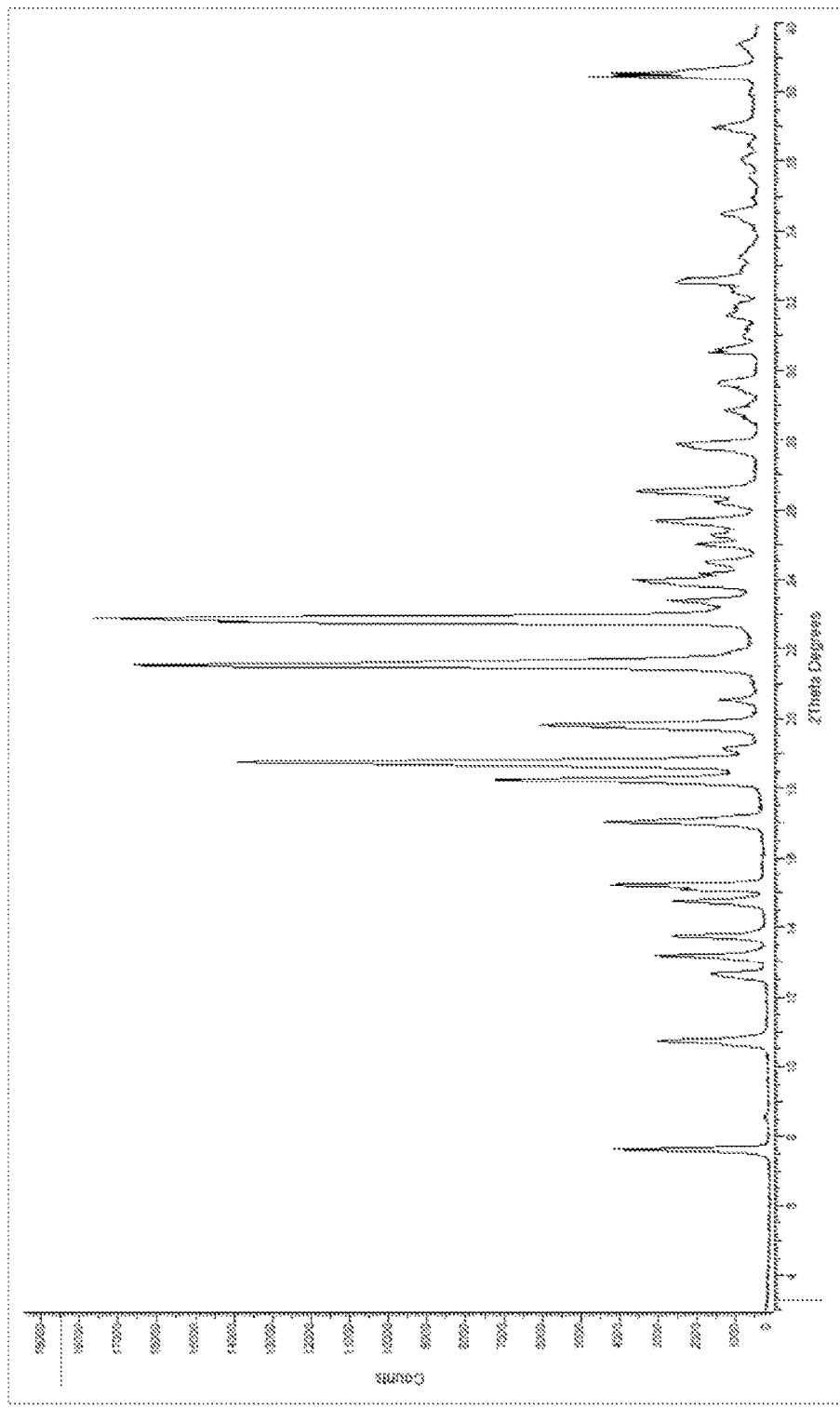
FIG. 4. PXRD pattern of crystalline glasdegib imidazole complex (1:1).

FIG. 4 shows PXRD data for the crystalline glasdegib imidazole complex (1:1), collected according to General Method 1.

Example 2

Preparation of 1-((2R,4R)-2-(1H-benzo[d]imidazol-2-yl)-1-methylpiperidin-4-yl)-3-(4-cyanophenyl)urea maleate (Form 1)

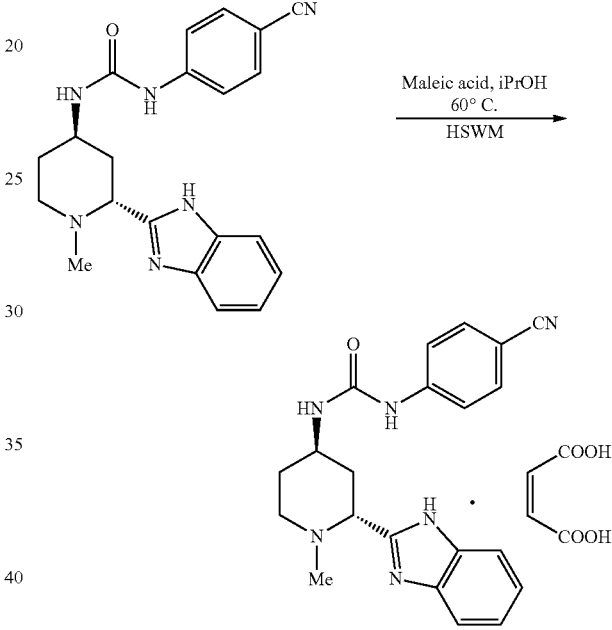

Into 1 L reactor, equipped with an overhead stirrer and High Shear Wet Mill (HSWM), was added 1-((2R,4R)-2-(1H-benzo[d]imidazol-2-yl)-1-methylpiperidin-4-yl)-3-(4-cyanophenyl)urea free base (38.2 g; 102 mmol) (prepared as described by Munchhof et al., *Med. Chem., Lett,* 2012, 3:106-111) and isopropanol (988 mL; 26 mL/g). The slurry was then heated to 60° C. to obtain a clear solution. A solution of maleic acid in isopropanol was separately prepared by dissolving maleic acid (14.28 g; 123 mmol; 1.2 equiv) in isopropanol (115 mL; 3 mL/g). While the HSWM was running (3200-8500 rpm), 20% of the maleic acid solution was added and the reaction maintained until the solution turned hazy. The HSWM was slowed down (3500 rpm) and the rest of the maleic acid solution was added over 1 hour. After aging the slurry for 1 hour at 60° C., the batch was cooled to 10° C. over 2 hours and granulated overnight. The solids were isolated by filtration, washed and dried at 60° C. The title compound (40.1 g; 801 mmol) was isolated as a white to off-white powder in 80% yield. $^1$H NMR (400 MHz, DMSO-d$_6$) δ 9.00 (s, 1H), 7.70 (d, J=8.8 Hz, 2H), 7.62 (dd, J=6.0, 3.3 Hz, 2H), 7.57 (d, J=8.8 Hz, 2H), 7.25 (dd, J=6.1, 3.2 Hz, 2H), 6.73 (d, J=7.5 Hz, 1H), 6.08 (s, 2H), 4.40 (s, 1H), 3.91 (d, J=11.5 Hz, 1H), 3.44 (d, J=12.2 Hz, 1H), 3.19 (s, 1H), 2.53 (s, 3H), 2.35 (d, J=13.2 Hz, 1H), 2.08 (d, J=13.3 Hz, 1H), 1.91 (q, J=12.4 Hz, 1H), 1.79 (q, J=12.4 Hz, 1H); $^{13}$C NMR (101 MHz, DMSO) δ 168.0, 154.7, 105.0, 145.3, 138.4, 135.6, 133.7, 123.0, 119.9, 118.0, 115.9, 103.1, 57.9, 50.5, 41.9, 41.7, 34.6, 28.0.

Example 3

Preparation of 1-((2R,4R)-2-(1H-benzo[d]imidazol-2-yl)-1-methylpiperidin-4-yl)-3-(4-cyanophenyl)urea maleate (Form 1)

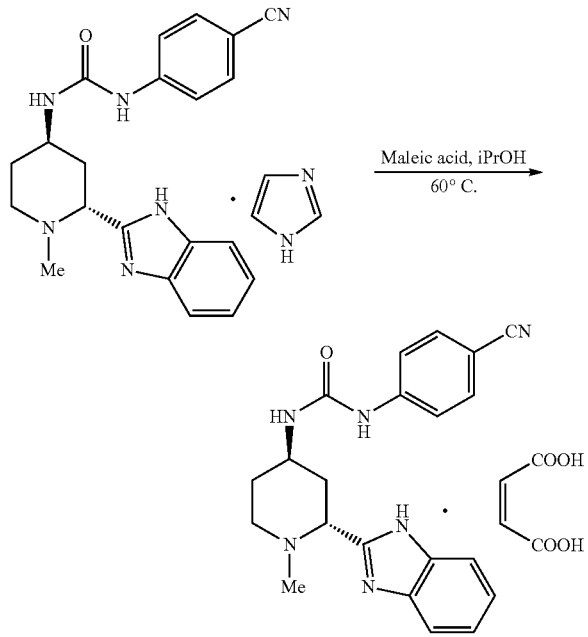

Into a 250 mL Flexy cube reactor equipped with an overhead stirrer, was added 1-((2R,4R)-2-(1H-benzo[d]imidazol-2-yl)-1-methylpiperidin-4-yl)-3-(4-cyanophenyl)urea imidazole complex (1:1) (7 g, 15.8 mmol) and isopropanol (140 mL; 20 mL/g of imidazole complex). The slurry was heated to 60° C. and held until a clear solution was obtained. A solution of maleic acid (34.8 mmol, 2.2 equiv) in aq. isopropanol (1% w/w) was prepared separately. Thirty percent of the maleic acid solution was added and the mixture was stirred for 5 min. Glasdegib maleate (77.6 mgs, 1%) was added as a seed, followed by the remainder of the maleic acid solution over 30 min. After aging at 60° C. for 30 min, the slurry was cooled to 20° C. over 60 minutes and granulated for an additional 60 min. After sonicating for 3 min, the slurry was filtered, washed with isopropanol (16 mL), followed by water washes (2×31 mL). The solids were dried in the oven at 60° C. for 12 hours to give glasdegib maleate (Form 1) (15.1 mmol, 7.40 g) as a tan powder in 95.4% yield with >98% purity. $^1$H NMR (400 MHz, DMSO-d$_6$) δ 9.00 (s, 1H), 7.70 (d, J=8.8 Hz, 2H), 7.62 (dd, J=6.0, 3.3 Hz, 2H), 7.57 (d, J=8.8 Hz, 2H), 7.25 (dd, J=6.1, 3.2 Hz, 2H), 6.73 (d, J=7.5 Hz, 1H), 6.08 (s, 2H), 4.40 (s, 1H), 3.91 (d, J=11.5 Hz, 1H), 3.44 (d, J=12.2 Hz, 1H), 3.19 (s, 1H), 2.53 (s, 3H), 2.35 (d, J=13.2 Hz, 1H), 2.08 (d, J=13.3 Hz, 1H), 1.91 (q, J=12.4 Hz, 1H), 1.79 (q, J=12.4 Hz, 1H); $^{13}$C NMR (101 MHz, DMSO) δ 168.0, 154.7, 105.0, 145.3, 138.4, 135.6, 133.7, 123.0, 119.9, 118.0, 115.9, 103.1, 57.9, 50.5, 41.9, 41.7, 34.6, 28.0.

Characterization of Glasdeqib Maleate (Form 1)

PXRD Data

FIG. 1 shows PXRD data for the crystalline glasdegib maleate (Form 1), collected according to General Method 1. A list of PXRD peaks at diffraction angles 2-Theta° (°2θ) ±0.2 °2θ and their relative intensities is provided in Table 1. Characteristic PXRD peak positions are indicated by an asterisk.

TABLE 1

PXRD peak list for glasdegib maleate (Form 1) (2-Theta °).

| Angle °2θ ± 0.2 °2θ | Relative Intensity % |
|---|---|
| 9.8 | 3 |
| 10.4 | 13 |
| 11.6* | 34 |
| 12.1* | 30 |
| 12.6 | 9 |
| 14.2 | 2 |
| 15.8 | 16 |
| 17.0* | 42 |
| 17.3* | 33 |
| 17.7* | 22 |
| 18.0 | 10 |
| 18.4 | 13 |
| 19.6* | 100 |
| 20.9 | 3 |
| 21.3 | 11 |
| 22.1 | 8 |
| 23.0 | 7 |
| 23.9 | 5 |
| 24.3 | 14 |
| 24.7 | 7 |
| 25.0 | 6 |
| 25.3 | 8 |
| 25.8 | 5 |

FT-Raman Data

FIG. 2 shows FT-Raman spectrum for the crystalline glasdegib maleate (Form 1), collected according to General Method 2. A list of FT-Raman peaks (cm$^{-1}$) and qualitative intensities is provided in Table 2 in cm$^{-1}$±2 cm$^{-1}$. Characteristic FT-Raman peaks (cm$^{-1}$) peaks are indicated by an asterisk. Normalized peak intensities are indicated as follows: w=weak; m=medium; s=strong.

TABLE 2

Full Raman Spectrum Peak list for glasdegib maleate (Form 1)

| Wave number cm$^{-1}$ ± 2 cm$^{-1}$ | Normalized peak intensity |
|---|---|
| 107 | m |
| 128 | m |
| 201 | w |
| 280 | w |
| 327 | w |
| 375 | w |
| 400 | w |
| 421 | w |
| 455 | w |
| 480 | w |
| 494 | w |
| 520 | w |
| 551 | w |
| 620* | w |
| 646 | w |
| 675 | w |
| 729 | w |
| 748 | w |
| 800 | w |

TABLE 2-continued

Full Raman Spectrum Peak list for glasdegib maleate (Form 1)

| Wave number cm$^{-1}$ ± 2 cm$^{-1}$ | Normalized peak intensity |
|---|---|
| 830* | w |
| 873 | w |
| 902 | w |
| 927 | w |
| 997* | w |
| 1014 | w |
| 1070 | w |
| 1113 | w |
| 1145 | w |
| 1175* | m |
| 1208* | w |
| 1233* | w |
| 1261* | w |
| 1273* | m |
| 1320 | w |
| 1329 | w |
| 1387 | w |
| 1432* | w |
| 1444* | w |
| 1463 | w |
| 1490 | w |
| 1534* | m |
| 1589* | w |
| 1612* | m |
| 1691* | w |
| 2168 | w |
| 2219* | s |
| 2932 | w |
| 2955* | w |
| 2976* | w |
| 3013* | w |
| 3029* | w |
| 3056 | w |
| 3116 | w | ssNMR Data

FIG. 3 shows the carbon CPMAS spectrum of crystalline glasdegib maleate (Form 1), which was collected according to General Method 3. Chemical shifts are expressed in parts per million (ppm) and are referenced to external sample of solid phase adamantane at 29.5 ppm. A list of ssNMR $^{13}$C chemical shifts (ppm) is provided in Table 3 in ppm±0.2 ppm. Characteristic ssNMR $^{13}$C chemical shifts (ppm) are indicated by an asterisk.

TABLE 3 ssNMR $^{13}$C Chemical Shifts for glasdegib maleate (Form 1) (ppm)

| $^{13}$C Chemical Shifts [ppm ± 0.2 ppm] | Relative Intensity (%) |
|---|---|
| 27.6 | 47 |
| 36.1 | 49 |
| 42.7 | 95 |
| 50.7 | 49 |
| 57.8* | 64 |
| 105.7 | 53 |
| 112.4 | 54 |
| 115.9 | 54 |
| 119.0 | 97 |
| 124.8 | 55 |
| 126.2 | 54 |
| 132.9 | 100 |
| 134.8* | 98 |
| 138.4 | 56 |
| 144.7* | 97 |
| 148.3 | 59 |
| 154.6 | 53 |
| 171.1 | 92 |

Example 4

Representative Drug Product Formulation of Glasdegib Maleate (Form 1)

A representative immediate release (IR) formulation of crystalline glasdegib maleate (Form 1) is provided in Table 4. Typical ranges for excipients in such formulations are provided in Table 5.

TABLE 4

Representative Composition of IR Tablet

| composition | | Quantity/unit (mg/tablet) | Wt % |
|---|---|---|---|
| glasdegib maleate (Form 1) | Active Ingredient | 32.765 | 26.2 |
| Microcrystalline Cellulose | Filler | 58.157 | 46.5 |
| Dibasic Calcium Phosphate Anhydrous | Filler | 29.078 | 23.3 |
| Sodium Starch Glycolate | Disintegrant | 3.750 | 3.0 |
| Magnesium Stearate (intra-granular) | Lubricant | 0.625 | 0.5 |
| Magnesium Stearate (extra-granular) | Lubricant | 0.625 | 0.5 |
| Total Tablet Weight | | 125.000 mg | 100 |

TABLE 5

Typical Ranges for IR Tablet Formulations

| composition | | Min. Wt % | Max. Wt % |
|---|---|---|---|
| glasdegib maleate (Form 1) | Active Ingredient | 16.383% | 32.765% |
| Microcrystalline Cellulose | Filler | 41.156% | 53.078% |
| Dibasic Calcium Phosphate Anhydrous | Filler | 20.578% | 26.539% |
| Sodium Starch Glycolate | Disintegrant | 3.000% | 3.000% |
| Magnesium Stearate | Lubricant | 1.000% | 2.500% |

PXRD Data

Table 6 provides a list of PXRD peaks at diffraction angles 2-Theta ° (°2θ)±0.2 °2θ and their relative intensities for the drug product containing crystalline glasdegib maleate (Form 1), collected according to General Method 1. Characteristic PXRD peak positions are indicated by an asterisk.

TABLE 6

PXRD peak list for glasdegib maleate (Form 1) drug product (2-Theta °). Asterisked peak positions represent characteristic peaks.

| Angle °2θ ± 0.2 °2θ | Relative Intensity % |
|---|---|
| 3.6 | 22 |
| 4.7 | 12 |
| 5.4 | 13 |
| 9.1 | 7 |
| 9.7 | 9 (API) |
| 10.4 | 16 (API) |
| 11.5* | 39 (API) |
| 12.1* | 27 (API) |
| 12.6 | 16 (API) |

TABLE 6-continued

PXRD peak list for glasdegib maleate (Form 1) drug product (2-Theta °). Asterisked peak positions represent characteristic peaks.

| Angle °2θ ± 0.2 °2θ | Relative Intensity % |
|---|---|
| 13.1 | 17 |
| 14.3 | 19 (API) |
| 14.9 | 21 |
| 15.8 | 32 (API) |
| 16.3 | 23 |
| 17.0* | 60 (API) |
| 17.3* | 42 (API) |
| 17.6* | 37 (API) |
| 18.0 | 24 (API) |
| 18.4 | 25 (API) |
| 19.6* | 99 (API) |
| 20.3 | 24 |
| 20.8 | 28 (API) |
| 21.3 | 35 (API) |
| 22.2 | 57 |
| 22.6 | 57 |
| 23.8 | 29 |
| 24.2 | 27 (API) |
| 24.7 | 22 |
| 25.3 | 22 |
| 25.5 | 22 |
| 26.6 | 83 |
| 27.2 | 100 (API) |
| 28.2 | 32 (API) |
| 28.5 | 31 |
| 28.9 | 24 |
| 30.2 | 86 |
| 30.5 | 46 |
| 31.0 | 17 |
| 32.5 | 33 |
| 32.8 | 40 |
| 33.5 | 17 |
| 34.1 | 16 |
| 34.6 | 19 |
| 35.0 | 20 |
| 35.4 | 16 |
| 36.0 | 23 |
| 37.3 | 16 |
| 37.7 | 16 |
| 38.3 | 14 |
| 39.1 | 16 |
| 25.3 | 22 |

Example 5

Preparation of 1-((2R,4R)-2-(1H-benzo[d]imidazol-2-yl)-1-methylpiperidin-4-yl)-3-(4-cyanophenyl)urea (S)-mandelate Salt

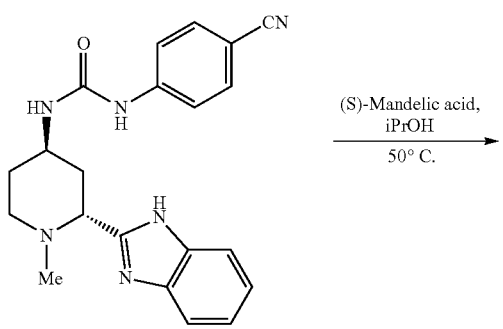

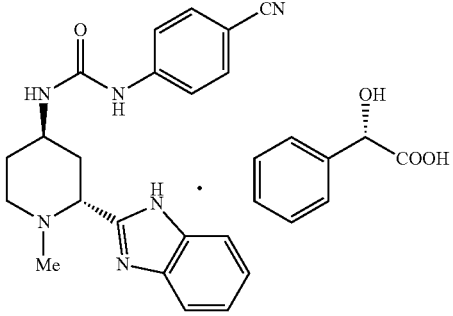

1-((2R,4R)-2-(1H-benzo[d]imidazol-2-yl)-1-methylpiperidin-4-yl)-3-(4-cyanophenyl)urea free base (318 mg, 0.85 mmol) was dissolved into 10 mL of isopropanol in a scintillation vial fitted with a stir bar. The solution was heated to 50° C. to ensure complete dissolution. To the solution was slowly added S-(+)-mandelic acid (~1.1 equiv) as a 30 mg/mL solution in isopropyl alcohol. After addition of a small amount of (S)-mandelate salt seed crystals, the solution became cloudy. The slurry was held at 50° C. for ~1 hour before being returned to room temperature and granulated for 12 hours. The resulting solids were isolated by filtration using a #2 Whatman filter and dried for 12 hours at 50° C. in a vacuum oven. Approximately 400 mg of glasdegib (S)-mandelate were prepared. The seed crystals were obtained by precipitation from a mixture of glasdegib free base, prepared as a stock solution in acetonitrile (~30 mg/mL), and S-(+)-mandelic acid as a solution of THF, which was stirred at rt overnight after heating at 60° C. for ~1 hour. The $^1$H NMR spectra was consistent with the (S)-mandelate salt.

Characterization of Glasdegib (S)-Mandelate Salt

The scaleup lot of the (S)-mandelate salt was analyzed by PXRD and Differential Scanning calorimetry (DSC). PXRD was obtained on a Bruker D8 X-Ray powder diffractometer with GADDS C2 system. Samples were scanned from ~6 to 38 degrees 2-theta for 60 seconds and oscillated 0.5 mm about the center. DSC was obtained on a TA DSC Q1000. The sample was heated at 10° C./min from 25° C. to 300° C.

PXRD Data

Figure 5:
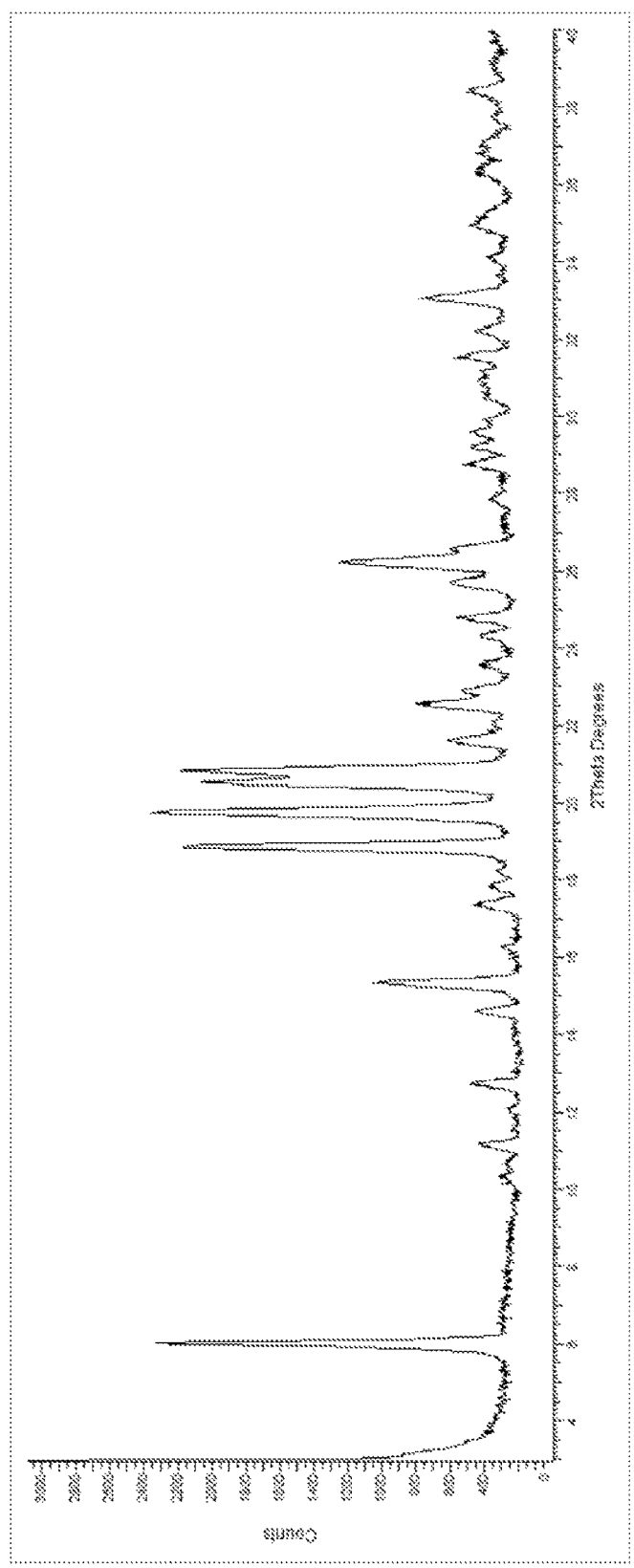
FIG. 5. PXRD pattern of crystalline glasdegib (S)-mandelate.

FIG. 5 shows PXRD data for the crystalline glasdegib (S)-mandelate, collected according to General Method 1.

DSC

The DSC thermogram displayed a sharp endotherm at 216° C.

Example 6

Comparative Stability Data

Comparative chemical and physical stability data was generated for tablet cores comprising glasdegib dihydrochloride monohydrate (diHCl.H$_2$O) and glasdegib maleate (Form 1) stored at 50° C./75% RH for 6 weeks. The tablet cores were prepared by dry granulation processing in a formulation composition comprising microcrystalline cellulose, dicalcium phosphate, sodium starch glycolate and magnesium stearate at an active drug loading level of 5%. The tablet cores were stored in open dish (no packaging) orientation in a 50° C./75% RH chamber and analyzed after 6 weeks of storage. The analytical testing included HPLC/Purity analysis and solid state NMR (for solid form).

TABLE 7

| Sample Description | Initial Level | 6 weeks @ 50° C./75% RH | Storage Recommendations | ssNMR Observations |
|---|---|---|---|---|
| Glasdegib dihydrochloride monohydrate (diHCl•H$_2$O) | Not detected | 2.75% | Desiccated storage required for drug product; 15-25° C. | Solid form conversion to amorphous |
| Glasdegib maleate (Form 1) | 0.024% | 0.55% | No special packaging required (no desiccant required); 15-25° C. | Consistent with the ingoing API solid form. |

The primary degradation product monitored is the epimeric 1-((2S,4R)-2-(1H-benzo[d]imidazol-2-yl)-1-methylpiperidin-4-yl)-3-(4-cyanophenyl)urea, which has the structure:

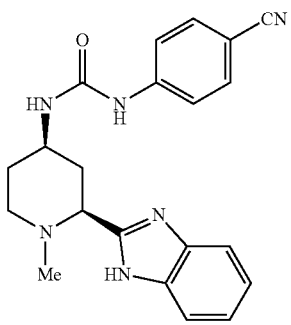 [SMILES: CN1CC[C@@H](NC(=O)Nc2ccc(C#N)cc2)C[C@H]1c1nc2ccccc2[nH]1]

A statistically designed 21-day stability study was performed for glasdegib maleate tablets and glasdegib dihydrochloride tablets containing 5% active drug loading. The design of the study is based on work in the literature that demonstrates the modeling degradation observed of solid oral dosage forms. See Waterman et al., *Pharmaceutical Research*, 24(4): 780-790 (2007). The tablets were stored in open glass bottles and exposed to various temperature, humidities and durations.

The recommended packaging for the glasdegib dihydrochloride monohydrate tablets is HDPE/IS Bottle, with desiccant. The labeled storage condition of this product is 15-25° C. Based on an accelerated stability study focusing on formation of the (2S,4R)-epimer with a target specification limit of NMT 0.5%, the shelf-life predicted for the glasdegib dihydrochloride monohydrate (60 cc HDPE bottle, 30 count tablets) at 25° C./60% RH is approximately 5 years with dessicant, and less than 2 years if stored without desiccant.

The recommended packaging for the glasdegib maleate tablets is HDPE/IS Bottle and no desiccant is required. The labeled storage condition of this product is 15-25° C. Based on the accelerated stability study focusing on formation of the (2S,4R)-epimer with a target specification limit of NMT 0.5%, the shelf-life predicted for glasdegib maleate (60 cc HDPE bottle, 30 count tablets) at 25° C./60% RH is more than 6 years stored without desiccant.

Example 7

Comparative Thermal Stability Data

Comparative thermal stability data was generated for glasdegib dihydrochloride monohydrate (diHCl.H$_2$O) and glasdegib maleate (Form 1). Differential Scanning calorimetry (DSC) measurements were performed with Discovery DSC (TA instruments) equipped with a refrigerated cooling accessory. All the experiments were performed in standard/Tzero aluminum pans. The cell constant was determined using indium and temperature calibration was performed using indium and tin as standards. All the measurements were done under continuous dry nitrogen purge (50 mL/min). Approximately 2-5 mg of solid sample was weighed into a standard/Tzero aluminum pan, sealed non-hermetically and heated from 25° C. to 250° C. at 10° C./min heating rate. The experimental data were analyzed using commercially available software (TA Universal Analysis 2000/Trios software, TA Instruments).

Based on the observed thermal stability data, the diHCl monohydrate solid form may be unstable under certain isolation and storage conditions due to the low dehydration temperature. The maleate form appears stable across a wide temperature range. The high level of form stability for the maleate salt may provide improved control in processing, handling, manufacture and storage for this form.

TABLE 8

Comparative thermal stability data

| Form | Thermal Stability | Remarks |
|---|---|---|
| Glasdegib maleate (Form 1) | Stable up to 207° C. (melting onset) | |
| Glasdegib dihydrochloride monohydrate | Stable up to 50° C. | Broad endotherm at 50° C. coincides with loss of water |

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

We claim:

1. A crystalline form of 1-((2R,4R)-2-(1H-benzo[d]imidazol-2-yl)-1-methylpiperidin-4-yl)-3-(4-cyanophenyl)urea maleate, having the structure:

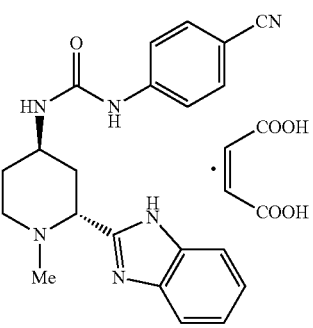

and having a powder X-ray diffraction pattern comprising peaks at 2θ values of: 11.6, 12.1 and 19.6° 2θ±0.2° 2θ.

2. The crystalline form of claim 1, having a powder X-ray diffraction pattern comprising peaks at 2θ values of: 11.6, 12.1, 17.0, 17.7 and 19.6° 2θ±0.2° 2θ.

3. The crystalline form of claim 1, having a Raman spectrum comprising a wavenumber ($cm^{-1}$) value of: 2219 $cm^{-1}$±2 $cm^{-1}$.

4. The crystalline form of claim 1, having a Raman spectrum comprising a wavenumber ($cm^{-1}$) value of: 1612 $cm^{-1}$±2 $cm^{-1}$.

5. The crystalline form of claim 1, having a Raman spectrum comprising wavenumber ($cm^{-1}$) values of: 1612 and 2219 $cm^{-1}$±2 $cm^{-1}$.

6. The crystalline form of claim 1, having a Raman spectrum comprising wavenumber ($cm^{-1}$) values of: 1534, 1612 and 2219 $cm^{-1}$±2 $cm^{-1}$.

7. The crystalline form of claim 1, having a Raman spectrum comprising wavenumber ($cm^{-1}$) values of: 1175, 1534, 1612 and 2219 $cm^{-1}$±2 $cm^{-1}$.

8. The crystalline form of claim 1, having a $^{13}C$ solid state NMR spectrum comprising a resonance (ppm) value of: 148.3 ppm±0.2 ppm.

9. The crystalline form of claim 1, having a $^{13}C$ solid state NMR spectrum comprising resonance (ppm) values of: 57.8, 134.8 and 148.3 ppm±0.2 ppm.

10. The crystalline form of claim 1, having a $^{13}C$ solid state NMR spectrum comprising resonance (ppm) values of: 57.8, 134.8, 144.7 and 148.3 ppm±0.2 ppm.

11. A crystalline form of 1-((2R,4R)-2-(1H-benzo[d]imidazol-2-yl)-1-methylpiperidin-4-yl)-3-(4-cyanophenyl)urea maleate, having the structure:

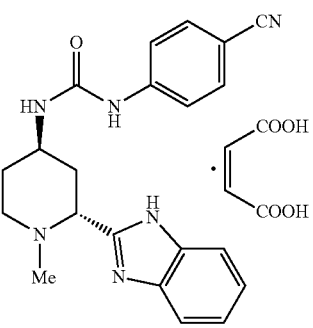

and having: (a) a powder X-ray diffraction pattern comprising peaks at 2θ values of: 11.6 and 12.1° 2θ±0.2° 2θ; and (b) a Raman spectrum comprising wavenumber ($cm^{-1}$) values of: 1612 and 2219 $cm^{-1}$±2 $cm^{-1}$.

12. A crystalline form of 1-((2R,4R)-2-(1H-benzo[d]imidazol-2-yl)-1-methylpiperidin-4-yl)-3-(4-cyanophenyl)urea maleate, having the structure:

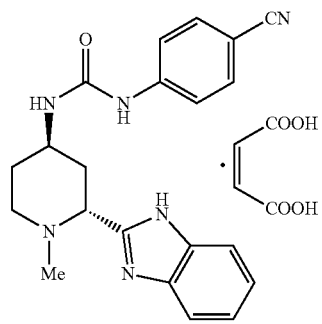

and having: (a) a powder X-ray diffraction pattern comprising peaks at 2θ values of: 11.6 and 12.1° 2θ±0.2° 2θ; (b) a Raman spectrum comprising wavenumber ($cm^{-1}$) values of: 1612 and 2219 $cm^{-1}$±2 $cm^{-1}$; and (c) a $^{13}C$ solid state NMR spectrum comprising a resonance (ppm) value of: 148.3 ppm±0.2 ppm.

13. The crystalline form of claim 1, having: (a) a Raman spectrum comprising wavenumber ($cm^{-1}$) values of: 1612 and 2219 $cm^{-1}$±2 $cm^{-1}$; and (b) a $^{13}C$ solid state NMR spectrum comprising a resonance (ppm) value of: 148.3 ppm±0.2 ppm.

14. A crystalline form of 1-((2R,4R)-2-(1H-benzo[d]imidazol-2-yl)-1-methylpiperidin-4-yl)-3-(4-cyanophenyl)urea maleate, having the structure:

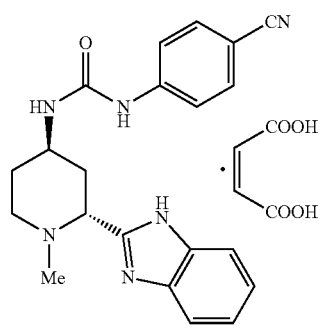

and having: (a) a powder X-ray diffraction pattern comprising peaks at 2θ values of: 11.6 and 12.1° 2θ±0.2° 2θ; and (b) a $^{13}C$ solid state NMR spectrum comprising a resonance (ppm) value of: 148.3 ppm±0.2 ppm.

15. A pharmaceutical composition comprising the crystalline form of claim 1, and a pharmaceutically acceptable carrier or excipient.

16. A pharmaceutical composition comprising the crystalline form of claim 11, and a pharmaceutically acceptable carrier or excipient.

17. A pharmaceutical composition comprising the crystalline form of claim 12, and a pharmaceutically acceptable carrier or excipient.

18. A pharmaceutical composition comprising the crystalline form of claim 14, and a pharmaceutically acceptable carrier or excipient.

* * * * *